United States Patent
Muller et al.

(10) Patent No.: US 10,629,305 B2
(45) Date of Patent: Apr. 21, 2020

(54) METHODS AND APPARATUS FOR SELF-LEARNING CLINICAL DECISION SUPPORT

(71) Applicant: General Electric Company, Schenectady, NY (US)

(72) Inventors: Serge Muller, Buc (FR); Axel Crasemann, München (DE); Marco Blumenthal, München (DE); Sylvain Bernard, Buc (FR); Razvan Iordache, Buc (FR)

(73) Assignee: General Electric Company, Schenectady, NY (US)

( * ) Notice: Subject to any disclaimer, the term of this patent is extended or adjusted under 35 U.S.C. 154(b) by 47 days.

(21) Appl. No.: 15/808,536

(22) Filed: Nov. 9, 2017

(65) Prior Publication Data

US 2019/0138693 A1 May 9, 2019

(51) Int. Cl.

| | |
|---|---|
| *G16H 50/20* | (2018.01) |
| *G06T 7/00* | (2017.01) |
| *G16H 50/70* | (2018.01) |
| *G06N 3/02* | (2006.01) |
| *G06N 5/04* | (2006.01) |

(52) U.S. Cl.
CPC .............. *G16H 50/20* (2018.01); *G06N 3/02* (2013.01); *G06T 7/0012* (2013.01); *G16H 50/70* (2018.01); *G06N 5/04* (2013.01); *G06T 2207/20081* (2013.01); *G06T 2207/20084* (2013.01)

(58) Field of Classification Search
CPC .......... G16H 50/20; G16H 50/70; G06N 3/02; G06N 5/04; G06T 7/0012; G06T 2207/20084; G06T 2207/20081
See application file for complete search history.

(56) References Cited

U.S. PATENT DOCUMENTS

| | | | |
|---|---|---|---|
| 8,296,247 B2 * | 10/2012 | Zhang | G06N 7/005 706/12 |
| 8,452,379 B2 | 5/2013 | DeFreitas et al. | |
| 2003/0120458 A1 * | 6/2003 | Rao | G06F 16/30 702/181 |
| 2005/0010445 A1 * | 1/2005 | Krishnan | G06F 19/321 705/2 |
| 2010/0138240 A1 * | 6/2010 | Leib | G06F 19/321 705/3 |
| 2016/0183901 A1 | 6/2016 | Bernard | |
| 2017/0200268 A1 * | 7/2017 | Podilchuk | G06K 9/6232 |

* cited by examiner

*Primary Examiner* — Jon Chang
(74) *Attorney, Agent, or Firm* — Hanley, Flight and Zimmerman, LLC

(57) ABSTRACT

Apparatus, systems, and methods for computer-aided detection are disclosed and described. An example apparatus includes at least one processor and a memory. The example memory includes instructions which, when executed, cause the at least one processor to at least: associate first patient data and first outcome data according to a set of association rules; train a processing model using machine learning and the associated first patient data and first outcome data; generate a computer-aided decision processing algorithm using the processing model; update the computer-aided decision processing algorithm based on at least one of second patient data or second outcome data received from a cloud infrastructure; and deploy the updated computer-aided decision processing algorithm to be applied to third patient data.

20 Claims, 10 Drawing Sheets

METHODS AND APPARATUS FOR SELF-LEARNING CLINICAL DECISION SUPPORT

FIELD OF THE DISCLOSURE

This disclosure relates generally to clinical decision support, and, more particularly, to methods and apparatus for self-learning clinical decision support.

BACKGROUND

X-ray imaging systems have become a valuable tool in medical applications such as for the diagnosis of many diseases. As standard screening for breast cancer mammography, for example, two-dimensional (2D) x-ray images are taken across the entire breast tissue. These 2D mammograms are limited by tissue superimposition. That is, lesions may be masked by the tissue above or underneath them, and/or normal tissue structures may mimic appearance and/or behavior of a lesion in the 2D image data. In order to minimize limitations of standard 2D-mammography caused by tissue superimposition, digital breast tomosynthesis using digital receptors has been developed.

Digital tomosynthesis systems employ at least one x-ray tube, which is moved in a trajectory (e.g., an arc, line segment, circle, other trajectory) above a detector (e.g., stationary, movable such as to remain perpendicular and/or within an angular range of a line passing through a focal spot for the imaging system, etc.). In digital breast tomosynthesis (DBT), the volume information of an object of interest can be derived from a series of images, known as projection images or projections, which are taken at various angles using one or more x-ray sources. Objects of different heights in a breast display differently in the different projections. From the 2D projection images, three-dimensional (3D) volumes can be generated for review. The generated 3D volume portions offer advantages to overcome the limitations associated with tissue superimposition. During the adoption period of the tomosynthesis technology, the provision of the 2D mammography is still desired by the medical professional or radiologist, who wants to use existing expertise gained from reviewing 2D mammograms. Furthermore, archived 2D mammograms can be better compared with images obtained using the same technology than with images obtained using exclusively a new modality such as tomosynthesis.

To address the need for 2D mammograms besides the provision of the relatively recent tomosynthesis images, a combination acquisition of images can be performed. That is, both the known 2D mammography and digital breast tomosynthesis projections are acquired for the same object of interest. However, since the average dose from tomosynthesis imaging is approximately the same as the known mammogram 2D imaging, the radiation exposure is roughly doubled. Thus, there is a need to generate or acquire the information of known 2D mammograms without performing two examinations, in order to reduce the dose. There is a need for more accurate analysis of image information to generate a synthetic 2D image from the reconstructed DBT volume and/or the set of projections, for example.

Computer-aided diagnosis (CAD) can assist a healthcare practitioner in interpreting medical images. Using CAD, 3D volumes, 2D images, etc., can be processed to highlight suspicious areas of an image to offer input to support a decision made by the healthcare practitioner. There is a need for improved CAD to improve assistance to the healthcare practitioner for improved diagnosis and treatment of patients.

BRIEF SUMMARY

Systems, articles of manufacture, apparatus, and methods for self-learning clinical decision support are disclosed and described herein.

An example method includes associating, using at least one processor, first patient data and first outcome data according to a set of association rules. The example method includes training, using the at least one processor, a processing model using machine learning and the associated first patient data and first outcome data. The example method includes generating, using the at least one processor, a computer-aided decision processing algorithm using the processing model. The example method includes updating, using the at least one processor, the computer-aided decision processing algorithm based on at least one of second patient data or second outcome data. The example method includes deploying, using the at least one processor, the updated computer-aided decision processing algorithm to be applied to third patient data.

An example computer readable medium includes instructions which, when executed, cause at least one processor to at least associate first patient data and first outcome data according to a set of association rules. The example instructions, when executed, cause the at least one processor to at least train a processing model using machine learning and the associated first patient data and first outcome data. The example instructions, when executed, cause the at least one processor to at least generate a computer-aided decision processing algorithm using the processing model. The example instructions, when executed, cause the at least one processor to at least update the computer-aided decision processing algorithm based on at least one of second patient data or second outcome data. The example instructions, when executed, cause the at least one processor to at least deploy the updated computer-aided decision processing algorithm to be applied to third patient data.

An example apparatus includes at least one processor and a memory. The example memory includes instructions which, when executed, cause the at least one processor to at least associate first patient data and first outcome data according to a set of association rules. The example instructions, when executed, cause the at least one processor to at least train a processing model using machine learning and the associated first patient data and first outcome data. The example instructions, when executed, cause the at least one processor to at least generate a computer-aided decision processing algorithm using the processing model. The example instructions, when executed, cause the at least one processor to at least update the computer-aided decision processing algorithm based on at least one of second patient data or second outcome data received from a cloud infrastructure. The example instructions, when executed, cause the at least one processor to at least deploy the updated computer-aided decision processing algorithm to be applied to third patient data.

Figure 1:
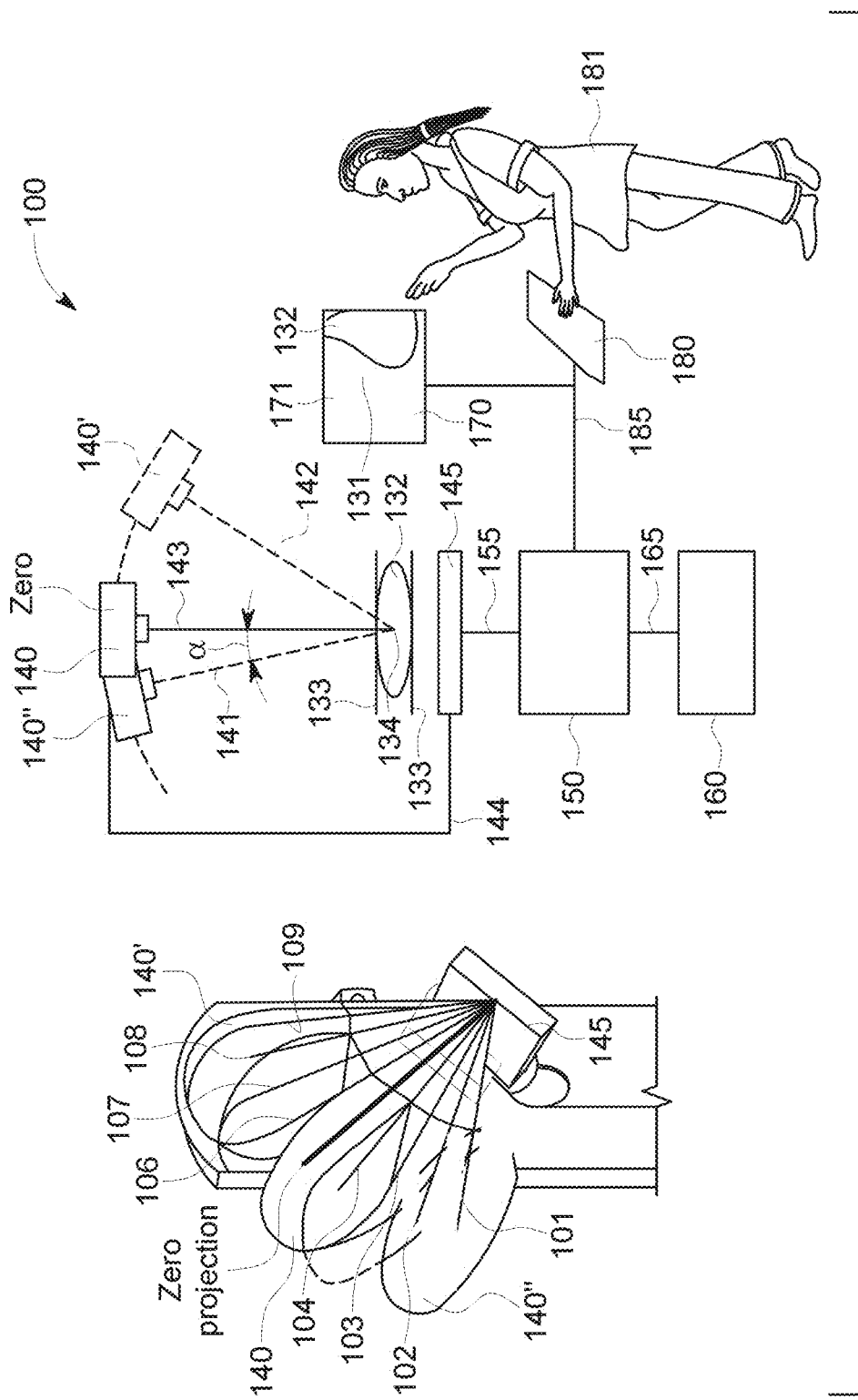
FIG. 1 illustrates an example imaging system.

The figures are not to scale. Instead, to clarify multiple layers and regions, the thickness of the layers may be enlarged in the drawings. Wherever possible, the same reference numbers will be used throughout the drawing(s) and accompanying written description to refer to the same or like parts. As used in this patent, stating that any part (e.g., a layer, film, area, or plate) is in any way positioned on (e.g., positioned on, located on, disposed on, or formed on, etc.) another part, means that the referenced part is either in contact with the other part, or that the referenced part is above the other part with one or more intermediate part(s) located there between. Stating that any part is in contact with another part means that there is no intermediate part between the two parts.

DETAILED DESCRIPTION

In the following detailed description, reference is made to the accompanying drawings that form a part hereof, and in which is shown by way of illustration specific examples that may be practiced. These examples are described in sufficient detail to enable one skilled in the art to practice the subject matter, and it is to be understood that other examples may be utilized. The following detailed description is therefore, provided to describe an exemplary implementation and not to be taken limiting on the scope of the subject matter described in this disclosure. Certain features from different aspects of the following description may be combined to form yet new aspects of the subject matter discussed below.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements.

As used herein, the terms "system," "unit," "module,", "engine,", "component," etc., may include a hardware and/or software system that operates to perform one or more functions. For example, a module, unit, or system may include a computer processor, controller, and/or other logic-based device that performs operations based on instructions stored on a tangible and non-transitory computer readable storage medium, such as a computer memory. Alternatively, a module, unit, or system may include a hard-wires device that performs operations based on hard-wired logic of the device. Various modules, units, engines, and/or systems shown in the attached figures may represent the hardware that operates based on software or hardwired instructions, the software that directs hardware to perform the operations, or a combination thereof.

While certain examples are described below in the context of medical or healthcare workplaces, other examples can be implemented outside the medical environment.

In recent years, deep learning techniques have utilized learning methods that allow a machine to be given raw data and determine the representations needed for data classification. Deep learning ascertains structure in data sets using back propagation algorithms which are used to alter internal parameters (e.g., node weights) of the deep learning machine. Deep learning machines can utilize a variety of multilayer architectures and algorithms. While machine learning, for example, involves an identification of features to be used in training the network, deep learning processes raw data to identify features of interest without the external identification.

Deep learning in a neural network environment includes numerous interconnected nodes referred to as neurons. Input neurons, activated from an outside source, activate other neurons based on connections to those other neurons which are governed by the machine parameters. A neural network behaves in a certain manner based on its own parameters. Learning refines the machine parameters, and, by extension, the connections or weight factors associated with the connections between neurons in the network, such that the neural network behaves in a desired manner.

Deep learning operates on the understanding that many datasets include high level features which include low level features. While examining an image, for example, rather than looking for an object, it is more efficient to look for edges which form motifs, which form parts, which form the object being sought. These hierarchies of features can be found in many different forms of data such as speech and text, etc.

An example use of deep learning techniques in the medical field is mammography. Mammography is used to screen for breast cancer and other abnormalities. Traditionally, mammograms have been formed on x-ray film. However, more recently, flat panel digital imagers have been introduced that acquire a mammogram in digital form, and thereby facilitate analysis and storage of the acquired images. Further, substantial attention and technological development have been dedicated toward obtaining three-dimensional images of the breast, using methods such as breast tomosynthesis. Breast tomosynthesis systems construct a 3D image volume from a series of 2D projection images, each projection image obtained at a different angular displacement of an x-ray source with respect to the detector. In certain examples, the x-ray source is stationary and the detector moves with respect to the source. The constructed 3D image volume is typically presented as a plurality of slices of image data, the slices being geometrically reconstructed on planes parallel to the imaging detector.

In certain examples, at least one enhanced image of an object of interest can be obtained based on 2D image data captured using an imaging system including an x-ray source facing a detector. For example, a plurality of 2D tomosynthesis projection images are acquired of the object of interest in a plurality of orientations. Then, a selected 2D projection image of the plurality of projections is enhanced using at least a subset of the plurality of tomosynthesis projection images.

An accumulation process for each pixel (i,j) of the selected projection image can be a summation, averaging, and/or other non-linear combination, for example. In an example, values can be averaged among all the projections excluding a most contrasting value. By excluding the most contrasting value, artifacts introduced by highly contrasted objects are reduced.

In certain examples, a 2D projection image can be enhanced by accumulating values for each pixel (i,j) of the 2D projection image at a given height in at least one of the tomosynthesis projections. The accumulated values for each pixel can be ranked over a plurality of possible heights. The most likely height for each pixel (i,j) can be determined by selecting the maximum accumulated value and combining (i,j)'s level with the determined maximum values for each pixel (i,j). The level of pixel (i,j) or (i,j)'s level corresponds to a gray level intensity of pixel (i,j) in the image.

In certain examples, the most likely height of each pixel (i,j) is stored as a height map associated with the enhanced 2D projection image. In certain examples, the most likely height of each pixel (i,j) is obtained as a combination of maximum accumulated value and 3D marks provided by a computer-aided diagnosis (CAD) (also referred to as computer-aided detection, computer-assisted diagnosis, etc.) system or indicated by a user through a 3D review system. In other examples, 3D finding locations can be received as input. When a pixel (i,j) is part of at least one finding's projection (e.g., the projection being performed on the image to be enhanced), the height associated with (i,j) becomes the height of the finding. The height map is then modified accordingly based on the height of the finding. The value to be combined with the original (i,j)'s level becomes the accumulated value for the finding's height.

In certain examples, the selected projection image is the central projection (0°), which is the projection perpendicular to or closest to the perpendicular of the detector. The central projection has advantageously the same geometry as a known 2D mammogram. For example, if the object of interest is a patient's breast, a 2D breast overview comparable to a known 2D mammogram is provided.

In certain examples, deep learning and/or other machine learning, artificial intelligence, etc., can be applied to determine pixel (i,j) height. For example, a convolutional neural network (CNN) can be generated, trained, and deployed to determine pixel (i,j) height based on projection information for the selected 2D projection image. Deep learning that utilizes a CNN segments data using convolutional filters to locate and identify learned, observable features in the data. Each filter or layer of the CNN architecture transforms the input data to increase the selectivity and invariance of the data. This abstraction of the data allows the machine to focus on the features in the data it is attempting to classify and ignore irrelevant background information.

Alternatively or in addition to the CNN, a deep residual network can be used. In a deep residual network, a desired underlying mapping is explicitly defined in relation to stacked, non-linear internal layers of the network. Using feedforward neural networks, deep residual networks can include shortcut connections that skip over one or more internal layers to connect nodes. A deep residual network can be trained end-to-end by stochastic gradient descent (SGD) with backpropagation.

Deep learning operates on the understanding that many datasets include high level features which include low level features. While examining an image, for example, rather than looking for an object, it is more efficient to look for edges which form motifs, which form parts, which form the object being sought. These hierarchies of features can be found in many different forms of data such as speech and text, etc.

Learned observable features include objects and quantifiable regularities learned by the machine during supervised learning. A machine provided with a large set of well classified data is better equipped to distinguish and extract the features pertinent to successful classification of new data.

A deep learning machine that utilizes transfer learning may properly connect data features to certain classifications affirmed by a human expert. Conversely, the same machine can, when informed of an incorrect classification by a human expert, update the parameters for classification. Settings and/or other configuration information, for example, can be guided by learned use of settings and/or other configuration information, and, as a system is used more (e.g., repeatedly and/or by multiple users), a number of variations and/or other possibilities for settings and/or other configuration information can be reduced for a given situation.

An example deep learning neural network can be trained on a set of expert classified data, for example. This set of data builds the first parameters for the neural network, and this would be the stage of supervised learning. During the stage of supervised learning, the neural network can be tested whether the desired behavior has been achieved.

Once a desired neural network behavior has been achieved (e.g., a machine has been trained to operate according to a specified threshold, etc.), the machine can be deployed for use (e.g., testing the machine with "real" data, such as data not used during the training phase of the neural network, etc.). During operation, neural network classifications can be confirmed or denied (e.g., by an expert user, expert system, reference database, etc.) to continue to improve neural network behavior. The example neural network is then in a state of transfer learning, as parameters for classification that determine neural network behavior are updated based on ongoing interactions. In certain examples, the neural network can provide direct feedback to another process. In certain examples, the neural network outputs data that is buffered (e.g., via the cloud, etc.) and validated before it is provided to another process.

Deep learning machines using convolutional neural networks (CNNs) can be used for data analysis. Stages of CNN analysis can be used to evaluate and/or otherwise estimate height of a pixel (i,j) in image projection data, presence of a lesion in image data using CAD, etc.

Deep learning machines can provide computer aided detection support to improve image analysis, as well as computer aided diagnosis for a patient. Supervised deep learning can help reduce susceptibility to false classification, for example. Deep learning machines can utilize transfer learning when interacting with physicians to counteract the small dataset available in the supervised training. These deep learning machines can improve their computer aided diagnosis over time through training and transfer learning.

For example, computer-aided detection or diagnosis (CAD) is a technology combining elements of artificial intelligence and computer vision with radiological and pathology image processing. For example, CAD can be used to support preventive medical check-ups in mammography (e.g., diagnosis of breast cancer), the detection of polyps in the colon, and identification of lung cancer and/or different types of tumor. CAD systems can mark conspicuous structures and sections in image data (detection) and/or evaluate the conspicuous structures (diagnosis). For example, in mammography, CAD highlights microcalcification clusters and hyperdense structures in soft tissue. This allows a radiologist, for example, to draw conclusions about a condition of the pathology. Another application of CAD is to quantify an object such as the size of a tumor and/or the tumor's behavior in contrast medium uptake, for example. CAD can be based on pattern recognition and application of machine learning (e.g., artificial neural network, deep learning, etc.) to evaluate and identify patterns in image data. One or more feature extractors can be used with machine learning to identify and analyze features in image data for CAD, for example.

In some examples, feature extractors can be implemented using one or more processing algorithms measure characteristics of a structure represented by the image data, such as mean gray level, maximum and/or minimum value, strength of gradient, fractal dimension, contrast of gray levels, image entropy, compactness of contour, etc. A support vector machine (SVM) is a classifier that processes extracted features from the image data to identify a class (e.g., suspicious versus probably benign, etc.) to which the structure represented by the image data belongs.

Certain examples facilitate continuous or ongoing improvement of CAD through machine learning to improve image processing such as synthetic 2D image generation, etc.

FIG. 1 illustrates an example imaging system 100 for obtaining an enhanced projection image of an object of interest. The example system 100 includes an x-ray beam source 140 facing the detector 145. The x-ray beam source 140 and the detector 145 can be connected by an arm 144. An object of interest 132 can be placed between the detector 145 and the source 140. In the example of FIG. 1, the x-ray source 140 moves in an arc above a single detector 145. The detector 145 and a plurality of positions of the x-ray source 140' and 140" following an arc (see dashed line) are shown with dashed/solid lines and in a perspective partial view. In the arrangement shown in the example of FIG. 1, the detector 145 is fixed at the shown position and only the x-ray source 140 moves. The angle α is a projection angle enclosed by the zero-orientation and any other orientation such as 141 and 142. Using this configuration, multiple views of the breast (e.g., the object of interest 132) tissue can be acquired via the at least one x-ray source 140. The projection of lowest a or the projection closest to the zero-orientation is named the central projection or zero projection by approximation.

Still referring to FIG. 1, on the left side is shown a partial perspective view of the imaging system 100 including the detector 145 and the x-ray source 140. The different positions of the x-ray source 140, 140' and 140" are broadly depicted to illustrate the movement of the x-ray source 140. There are nine different projection views 101, 102, 102, 103, 104, 106, 107, 108, 109 including the zero projection 105 indicated as straight lines, which all point to the center of the detector 145.

The patient (not shown) is positioned in front of the mammography arm. To obtain, for example, a mediolateral oblique (MLO) view, the mammography technologist 181 sets the angle of the arm 144 for the desired projection (e.g., 30 degrees to 60 degrees, wherein 45 degree represents the preferred zero projection shown in the perspective view of FIG. 1).

An image 131 of the object of interest 132 shown in display unit 170 is the image of the breast compressed by compression plates 133, which help ensure uniform compression and immobilization of the breast during the radiation exposure for optimal image quality. The user may review calcifications or other clinical relevant structures for diagnosis, for example. The display 170 depicts a 2D mammography view, a projected view acquired during a DBT scan, a reconstructed slice reconstructed from the set of projections acquired during the DBT scan, etc.

The detector 145 and the x-ray source 140 form an acquisition unit, which is connected via a data acquisition line 155 to a processing unit 150. The processing unit 150 includes a memory unit 160, which may be connected via an archive line 165, for example.

A user such as a health professional may input control signals via a user interface 180. Such signals are transferred from the user interface 180 to the processing unit 150 via the signal line 185. Using the example system 100, an enhanced 2D projection image can be obtained that appears similar or close to a 2D mammogram. Based on this high quality image, a radiologist and/or other user can identify clinical signs relevant for breast screening. Further, historical, stored 2D mammograms can be displayed for comparison with the new 2D projection image acquired or synthesized through tomosynthesis. Tomosynthesis images may be reviewed and archived, and a CAD system, a user, etc., can provide 3D marks corresponding to the location of detected objects of interest. A height map of punctual objects or other objects obtained from image data can be combined with height information provided based on 3D marks by a CAD system, indicated by a user through a 3D review, etc. Further, the user may decide to archive 2D and/or full-volume images and/or other images. Alternatively, or in addition, saving and storing of the images may be done automatically.

In certain examples, the memory unit 160 can be integrated with and/or separated from the processing unit 150. The memory unit 160 allows storage of data such as the 2D enhanced projection image and/or tomosynthesis 3D images. In general, the memory unit 160 can include a computer-readable medium, such as a hard disk, a solid state drive (SDD) or a CD-ROM, diskette, a ROM/RAM memory, DVD, the computer-readable medium being physically attached to the processing unit 150 or accessible through wireless communication or through a network or the Internet, etc. The processing unit 150 is configured to execute program instructions stored in the memory unit 160, which cause the computer to perform methods and/or implement systems disclosed and described herein. One technical effect of performing the method(s) and/or implementing the system(s) is that the x-ray source may be less used, since the enhanced 2D projection image can replace a known 2D mammogram, which is usually obtained using additional x-ray exposures to get high quality images.

Figure 2:
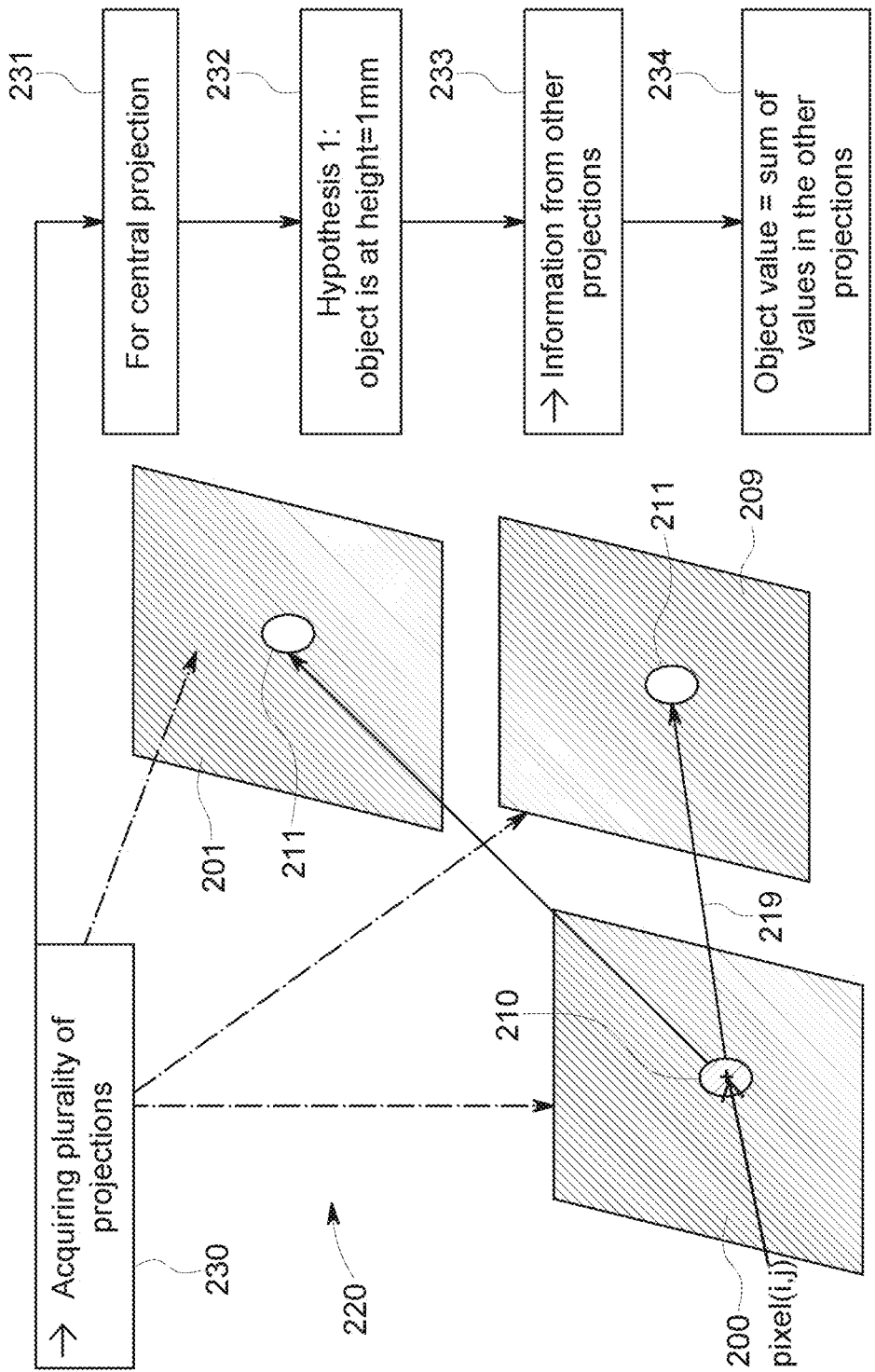
FIGS. 2-4 illustrate flow diagrams for example methods to obtain an enhanced image of an object of interest.

FIG. 2 illustrates a flow diagram for an example method 220 to determine object height in target tissue (e.g., breast tissue, etc.) based on image projection information. At block 230, a plurality of 2D projection images 200, 201, 209 are acquired (e.g., 9 projections, 10 projections, 5 projections, 20 projections, etc.). To generate an enhanced 2D projection image, at block 231, a central projection is selected. The central projection is selected to have the same or similar geometry as 2D mammograms. The central projection advantageously provides underlying breast content, for example.

Projection images may be acquired at a low dose, which can be many times lower than the dose needed for a 2D mammogram. This low dose results in low image quality, which needs to be improved or enhanced. In the central projection, the object 210 corresponding to the projection of a 3D object present in the breast is represented in 2D including a pixel (i,j). The pixel (i,j) is indicated with the cross in the center of the object 210 in the example of FIG. 2. Due to the 2D representation of the object 210, a height location of the corresponding 3D object within a volume of the breast is not known. The term "height" in this instance indicates a given altitude or distance of an object in the breast volume relative to or spaced away from a reference plane such as the detector entrance plane. Since the height of the 3D object associated with the object 210 is not known, at block 232, the height is guessed or estimated. As a first hypothesis (or starting point), a location of the 3D object associated with the object 210 is assumed to be at a height of 1 mm. Based on this hypothesis information, at block 233, at least a subset of the plurality of other projections is retrieved. This subset or other projections are illustrated schematically in the example of FIG. 2 by the projections 201 and 209.

At block 234, an object value is calculated by accumulating, adding, or summing the values of objects 211 found at 1 mm in the other projections 201, 209.

Figure 3:
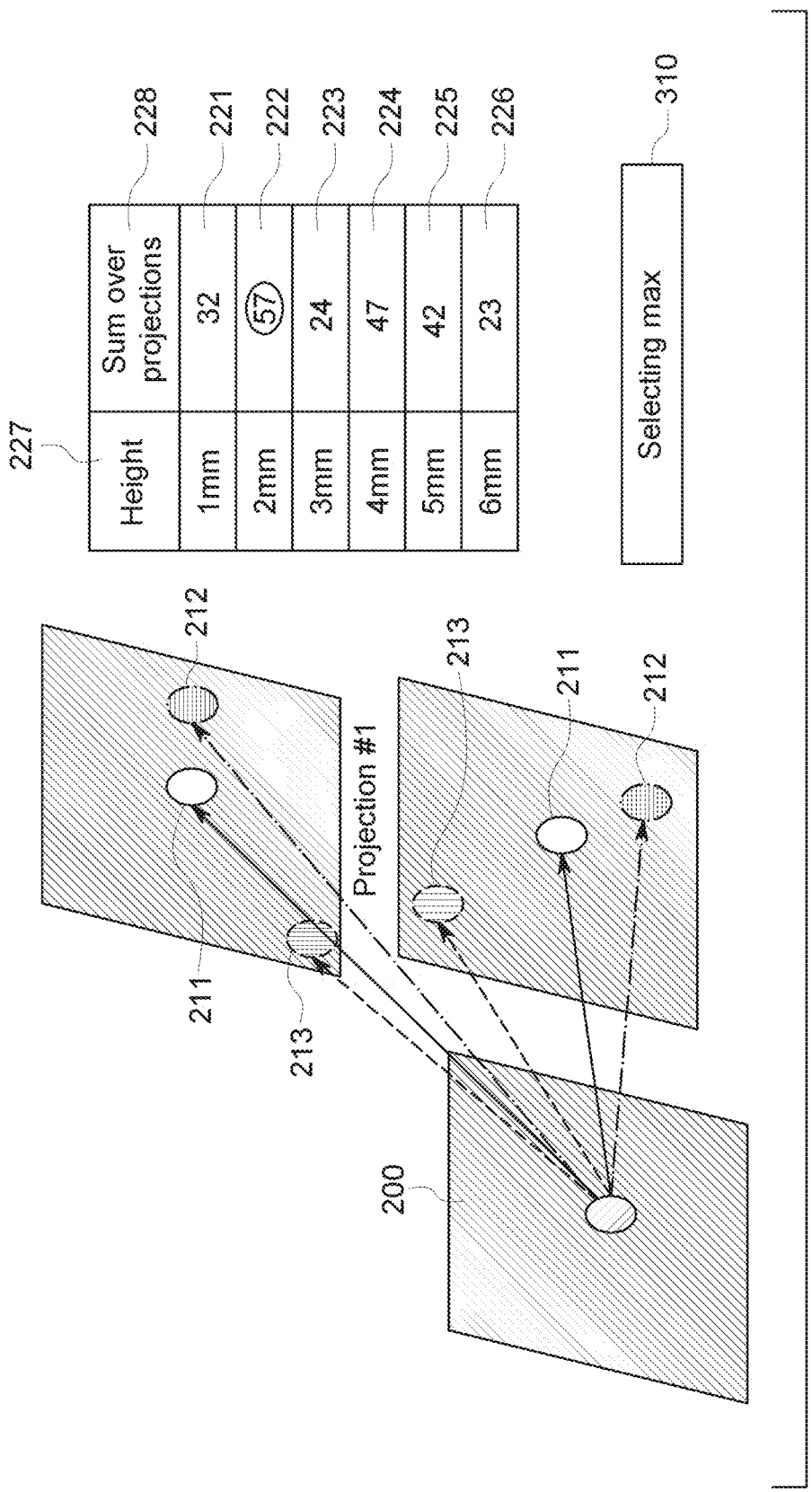

FIG. 3 provides further detail regarding an example implementation of block 234 of FIG. 2 using a height table to summarize pixel (i,j) height values. Similar to the first hypothesis of 1 mm, additional hypotheses are made for other heights in 1 mm steps or increments (e.g., 1 mm, 2 mm, 3 mm, etc.). The result of each hypothesis at a given height is depicted in a first column 227 including different height values. In a second column 228, sums of values in other projections 221, 222, 223, 224, 225, 226 are provided. The example method is schematically shown by the arrows originating from an object or pixel (i,j) and pointing to the corresponding values in other projections (201, 209). The sums are then derived from the values of objects 211, 212, 213 and corresponding pixel positions in the other projections.

As shown in the example of FIG. 3, at block 310, a maximum value is selected from the accumulated values. That is, by ranking the accumulated values for each pixel over possible heights, the most likely height for each pixel (i,j) can be determined. In this context, the term "most likely height" indicates an estimated or most probable height position or altitude for the breast structure projected on each pixel (ij). Since the method to obtain the most likely height is an estimation method, the resulting height is with very high probability the real height of the 3D object within the breast and projected on pixel (i,j). In the illustrated example of FIG. 3, the maximum value of 57 was determined at a height of 2 mm, such that the 3D object associated with the object 210 is most likely positioned at this height. From this information regarding the most likely heights of each pixel (i,j), a height map can be generated. The height map can be associated with an enhanced 2D projection image. The enhanced 2D projection image is obtained by combining the level of pixel (i,j) with the determined maximum values for each pixel (i,j).

As described further below, certain examples leverage artificial intelligence (e.g., machine learning, deep learning, etc.) to improve technology involved in pixel (i,j) height determination and object 210 detection accuracy.

Figure 4:
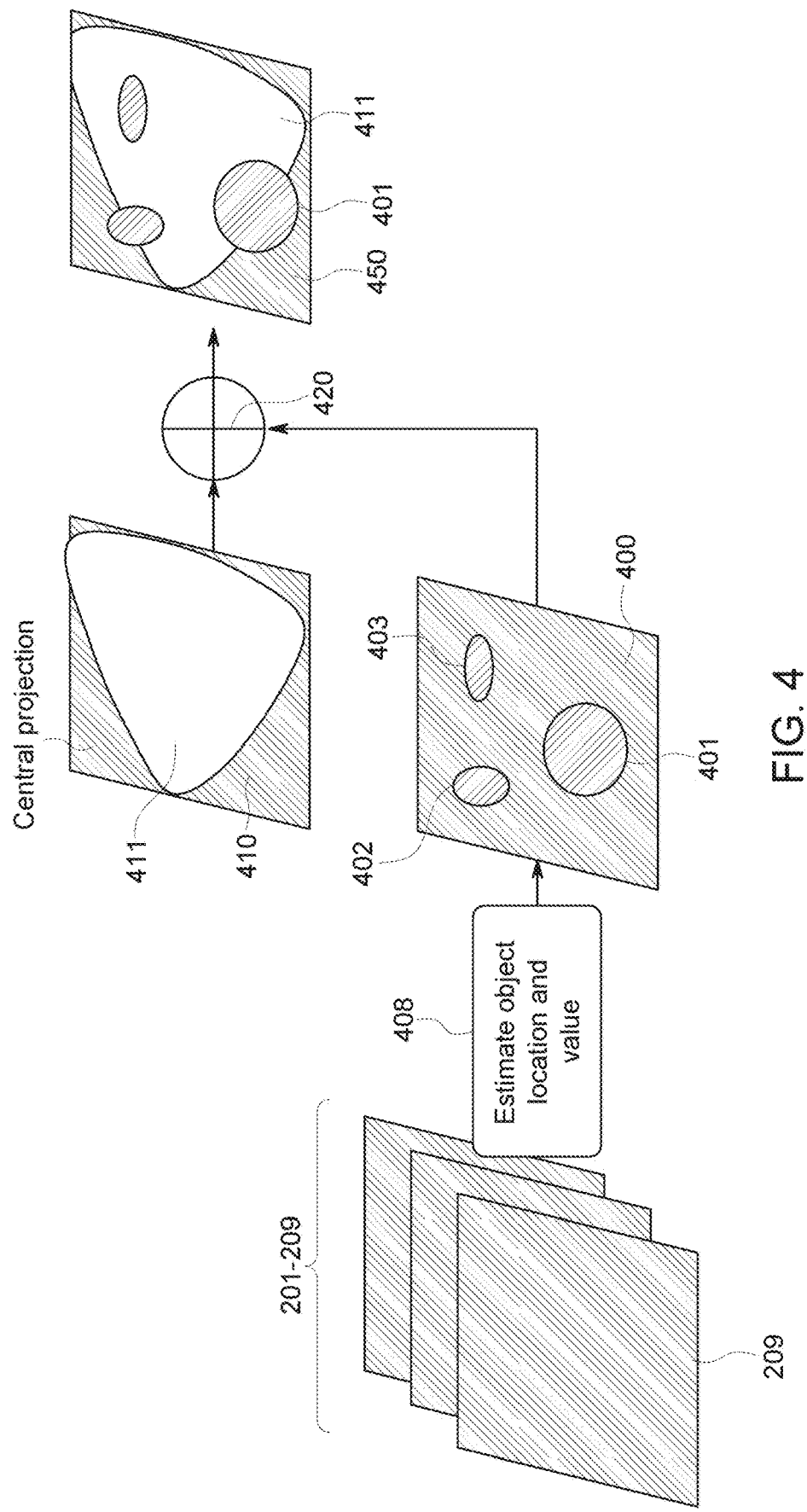

FIG. 4 shows a flow diagram of an example method to obtain an enhanced 2D projection image. Tomosynthesis projection image values (e.g., projections 200-209, etc.) is performed for different frequency bands corresponding to different object sizes to better image and identify small calcifications or bigger objects as masses in the tissue. At block 408, a 3D object location or height of a 2D object of a selected projection 200 and corresponding value is estimated based on information from other projections (201, . . . 209). Then, determination of the most likely height for each pixel follows by selecting the maximum accumulated value. A projection 400 provides top ranked object values for each pixel after the height determination. The projection 400 shows objects of different sizes, and the central projection 410 schematically shows image data of breast tissue 411.

At block 420, the central projection 410 is combined or blended with the projection 400. For example, the level of pixel (i,j) is combined with the determined maximum values for each pixel (i,j) to obtain an enhanced 2D projection image 450. The image 450 can be reviewed by a health professional, who can analyze objects of interest 401 and underlying tissue 411 for diagnosis.

Figure 5:
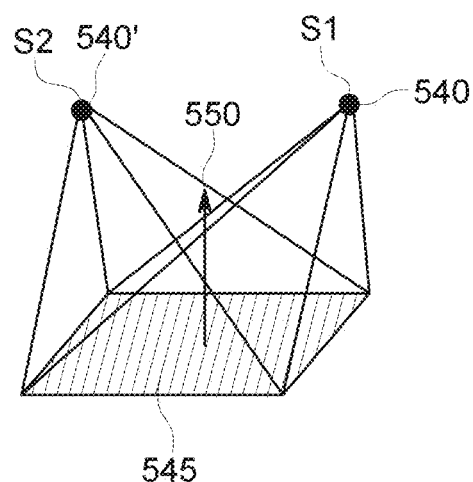
FIGS. 5-6 illustrate example acquisition geometries.

FIG. 5 shows an example source detector arrangement as used for example in FIG. 1. As shown in the example of FIG. 5, a detector 545 is stationary in relation to a source 540. The source 540 moves during the tomosynthesis acquisition from a source position S1 to a source position S2. An arrow 550 indicates a normal perpendicular to a detector plane and is situated in the center of the plane. The normal 550 points to the source 540 only in the zero projection.

Figure 6:
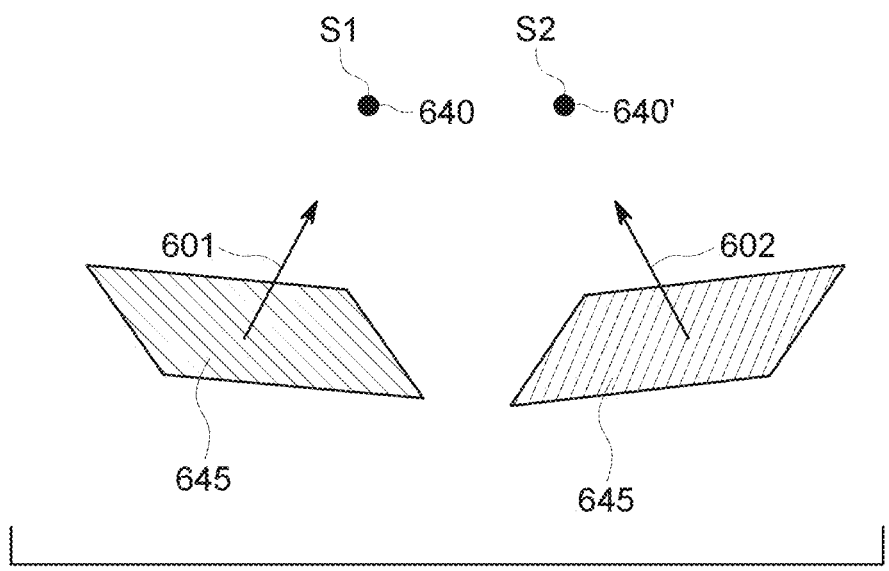

FIG. 6 shows an example diagrammatic illustration of an acquisition geometry according to another example. In the example of FIG. 6, a source 640 moves as in FIG. 5 from a source position S1 to a source position S2. However, the detector's central normal points at each position S1 and S2 to the source 640 and 640', respectively. This geometry can be provided by a virtual rotating detector. This virtual detector allows an improved rendering of the volume, since structure shifts from one projection to the other are limited.

In certain examples, each enhanced image projected on a perpendicular virtual projection can be displayed successively for review. To reduce artifacts and noise, the tomosynthesis projection images may further be filtered and/or denoised prior to enhancing or improving the image quality.

As discussed above, developing machine-learning based CAD systems may involve a large set of cases with known truth (e.g., lesions and/or other content of the images has been verified and the cases are able to be used for reference, etc.). "Truthed" cases are important in CAD for at least two reasons: development and registration. In development, a learning algorithm can be trained as part of the CAD, for example. In registration, evidence of performance (e.g., receiver operating characteristic (ROC) curves, etc.) can be provided to a regulatory agency such as the Food and Drug Administration (FDA), for example. For the manufacturer, case collection for training, etc., is long, costly, and painful process. Additionally, once a traditional CAD version is released, its operating point(s) and performance cannot be modified/improved. A new development/registration round has been necessary in prior approaches to update the CAD system and release a new version thereof.

As a result, CAD algorithms have faced cost and performance issues (e.g., especially for mass detection in x-ray breast imaging, etc.). Certain examples leverage deep learning technologies to improve CAD performances. However, deep learning technologies require much training data and computation power. Also, existing development paradigms prevent improving CAD performances at a fast pace, given that for each new version a complete training/release/registration cycle is involved in traditional/prior approaches. Consequently, CAD penetration rate remains low, especially when not supported by reimbursement policies as in Europe, compounded by false positive marks and low performance on identification of masses in image data.

Certain examples address these technological deficiencies by providing improved CAD technology including a continuous (or substantially continuous given some data collection, processing, transmission, and/or storage latency, etc.) improvement process enabled by a cloud architecture that provides a centralized database of training cases and a high computation power used by many learning technologies such as deep learning, etc.

Certain examples leverage radiologist feedback and systems to provide daily updates to enrich a learning database of truthed training cases, rather than relying on the manufacturer to collect and organize reference data. Such radiologist contributions can be update-to-date, relevant, and verified by experts to serve as interested truthed cases to train the CAD framework.

For example, when cancerous tissue is found in a patient, images, lesion position, and grade are sent to a centralized database (e.g., a data store, data lake, etc., in the cloud architecture). In certain examples, such information is sent together with demographic and clinical history of the patient. In some examples, an initial set of image data is obtained and then, when, for example, one-year follow-up data becomes available and the case is rated according to a severity scale such as the Breast Imaging-Reporting and Data System (BI-RADS) quality assurance scale as normal (BIRADS 1) or benign (BIRADS 2), the case from the previous year can be sent to the centralized database as a non-cancer case.

In certain examples, beyond enriching case collection, participating radiologists can identify CAD errors and/or provide other feedback to facilitate machine learning purpose by pointing out CAD false negatives, dismissing false positives, etc. The CAD system integrates the feedback in a truthed training set and retrains the CAD algorithm.

Before "releasing" or deploying updated CAD, validation is performed. The updated CAD version is first applied on a validation database, which is the "official database" used to compute the ROC performance of the CAD system for registration. If the performance is superior (or non-inferior) to performance of the previous CAD version, then the new CAD version replaces the previous CAD version as the CAD system to be used with incoming image data.

Certain examples provide an association processor to facilitate truthed data collection. The association processor is connected to the cloud architecture where patient data is archived. The association processor applies a set of association rules which define when patient data is to be collected to form a truthed case (e.g., a case composed of input data and outcomes verified). The truthed data is sent to a truthed database. The truthed database can then be used by a learning processor to update image data processing, for example.

Examples of truthed data obtained after association of data in the cloud architecture include input data and outcomes. Input data can include mammography or/and ultrasound images, radiologist report (e.g., location of findings, description of findings, etc.), breast density, images of tissue samples, initial visit oncologist report, follow-up visit oncologist reports, prescribed treatment, etc. Outcomes can include pathology reports, cancerous versus benign diagnosis, cancer grade, lesion localization, hormonal receptor status, treatment outcome, clinical outcomes (e.g., cured, recurrence, death, etc.), etc.

In certain examples, a learning or processing algorithm can correlate outputs with inputs. By correlating outputs with inputs, the learning/processing algorithm can detect lesions in an image, correlate input morphological information with output cancer grade, etc. For example, based on a shape of a potential lesion in input image data, the learning/processing algorithm can estimate a cancer grade associated with the lesion. The learning/processing algorithm can also correlate information from different input modalities with outputs from the learning cases in the truthed database.

In certain examples, a regular download (e.g., nightly, weekly, etc.) of the newly trained CAD system can assist radiologists benefiting from the best CAD performance. In certain examples, the FDA and/or other regulatory/supervisory body can be informed regularly (e.g., daily, weekly, etc.) regarding CAD performance through up-to-date ROC curves, etc.

In certain examples, processing (e.g., synthetic 2D image generation, etc.) using an underlying CAD system can benefit from the continuous improvement process described above. Certain examples provide continuous improvement of CAD algorithms by continuous update of the learning database with (truthed) cases from daily practice. Certain examples facilitate verification that CAD performance is non-inferior to the original CAD version approved by the FDA. Certain examples provide a scalable architecture in which the continuous update of the database can be done at hospital, regional, or national level.

As discussed above, certain examples leverage artificial intelligence (e.g., deep learning, other machine learning, etc.) to improve image processing and outcome determination (e.g., via CAD, etc.). For example, a neural network (e.g., a CNN, RNN, etc.) can be leveraged to gather data and improve image segmentation, object identification, outcome correlation, etc.

Figure 7:
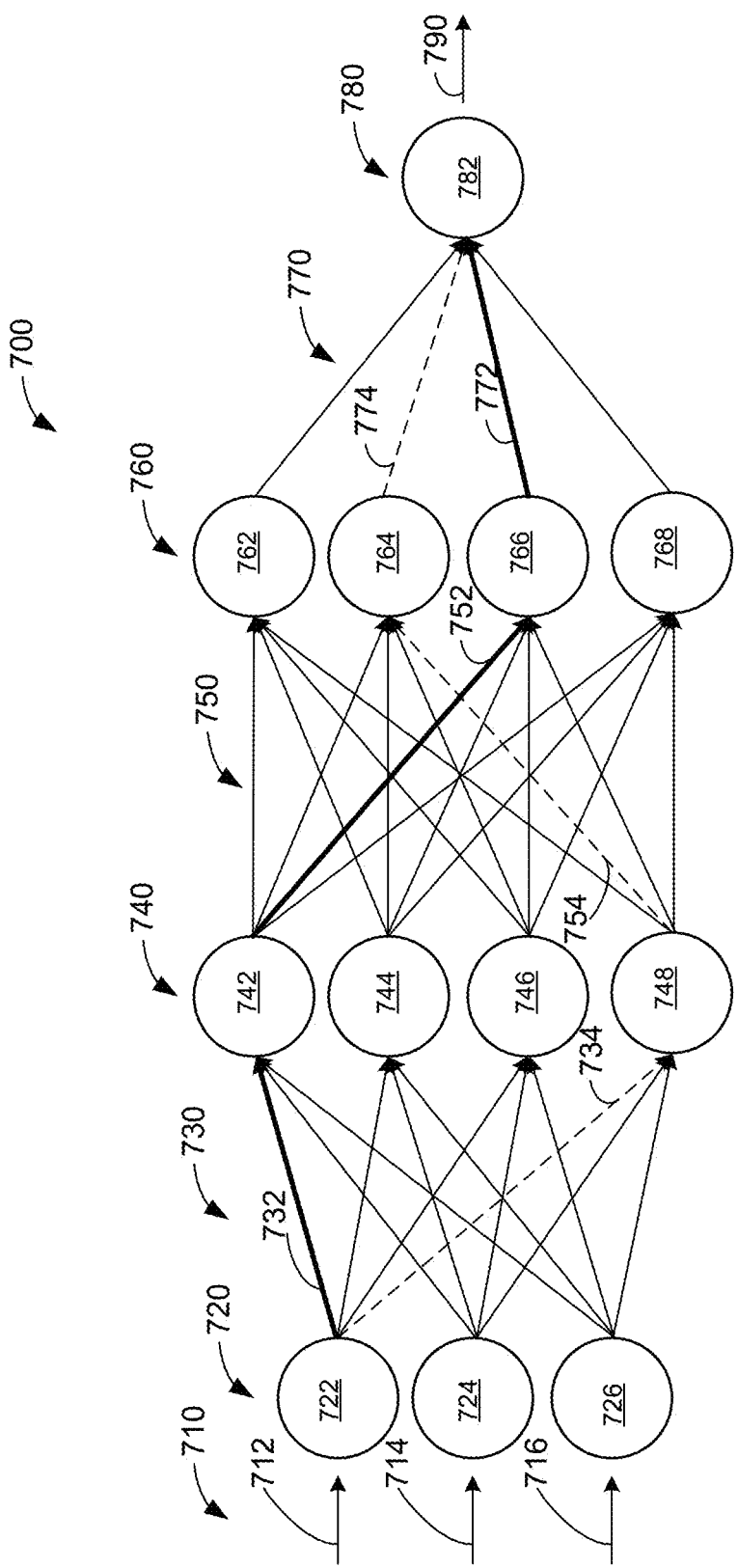
FIG. 7 illustrates an example neural network.

FIG. 7 is a representation of an example deep learning neural network 700 that can be used to improve CAD processing of image and related data. The example neural network 700 includes layers 720, 740, 760, and 780. The layers 720 and 740 are connected with neural connections 730. The layers 740 and 760 are connected with neural connections 750. The layers 760 and 780 are connected with neural connections 770. Data flows forward via an input set 710 including inputs 712, 714, 716 from the input layer 720 to the output layer 780 and to an output 790.

The layer 720 is an input layer that, in the example of FIG. 7, includes a plurality of nodes 722, 724, 726. The layers 740 and 760 are hidden layers and include, the example of FIG. 7, nodes 742, 744, 746, 748, 762, 764, 766, 768. The neural network 700 may include more or less hidden layers 740 and 760 than shown. The layer 780 is an output layer and includes, in the example of FIG. 7, a node 782 with an output 790. Each input 712-716 corresponds to a node 722-726 of the input layer 720, and each node 722-726 of the input layer 720 has a connection 730 to at least one node 742-748 of the hidden layer 740. Each node 742-748 of the hidden layer 740 has a connection 750 to at least one node 762-768 of the hidden layer 760. Each node 762-768 of the hidden layer 760 has a connection 770 to the output layer 780. The output layer 780 has an output 790 to provide an output from the example neural network 700.

Of connections 730, 750, and 770 certain example connections 732, 752, 772 may be given added weight while other example connections 734, 754, 774 may be given less weight in the neural network 700. Input nodes 722-726 are activated through receipt of input data via inputs 712-716, for example. Nodes 742-748 and 762-768 of hidden layers 740 and 760 are activated through the forward flow of data through the network 700 via the connections 730 and 750, respectively. Node 782 of the output layer 780 is activated after data processed in hidden layers 740 and 760 is sent via connections 770. When the output node 782 of the output layer 780 is activated, the node 782 outputs an appropriate value based on processing accomplished in hidden layers 740 and 760 of the neural network 700.

For example, inputs 712-716 can be provided with image data, related patient data, etc. Through nodes 740, 760, 780 and connections 730, 750, 770, inputs 712-716 can be converted to a diagnostic/predictive output 790 (e.g., objection identification such as lesion, cancerous tissue, etc.) to be provided to example CAD methods and systems to facilitate improved diagnosis and treatment.

Figure 8:
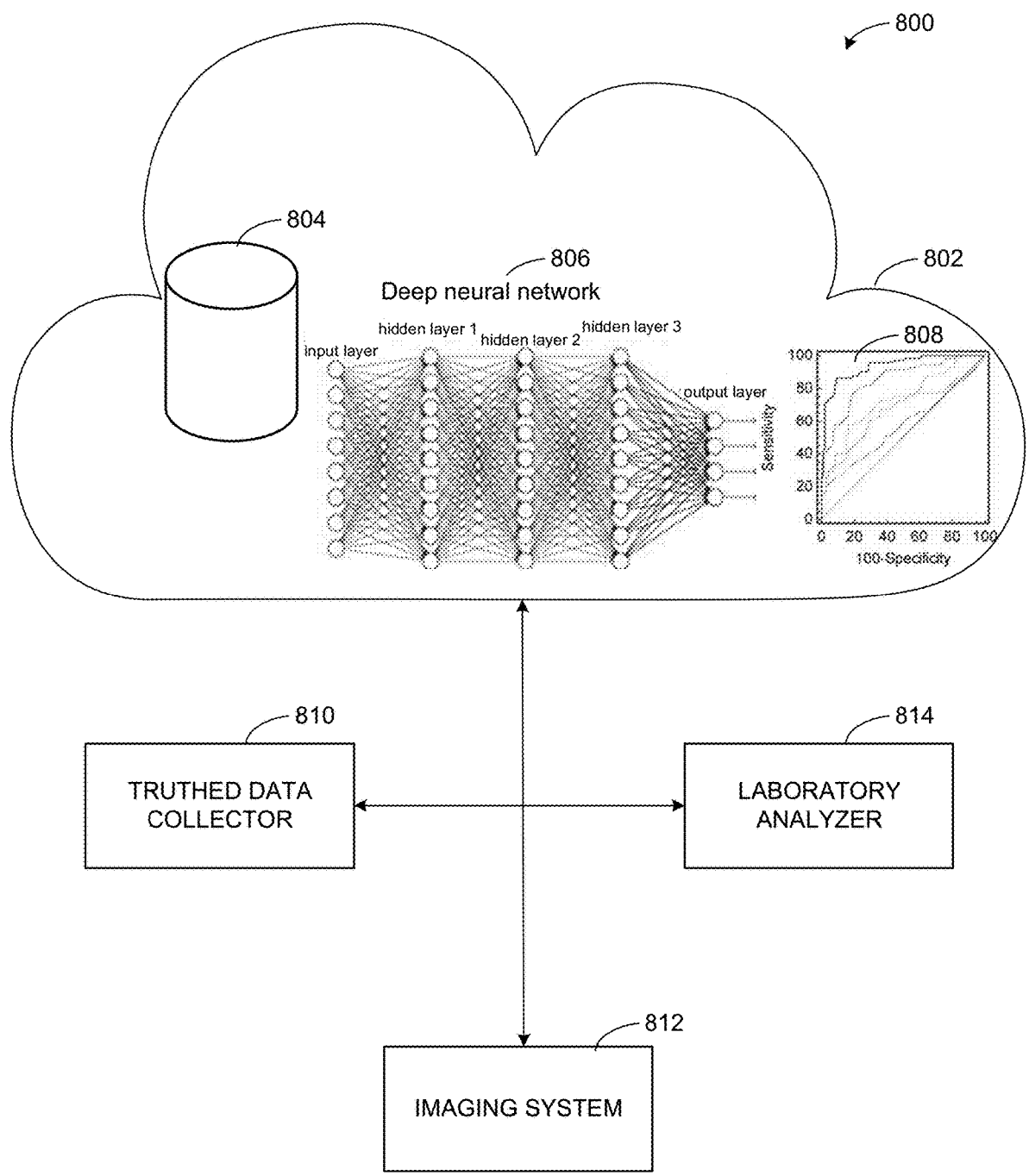
FIG. 8 illustrates an example system including a cloud architecture.

FIG. 8 illustrates an example system 800 including a cloud architecture 802 including a database 804, an artificial neural network and/or other machine learning network 806, and an output 808 (e.g., a performance report, CAD output, etc.). Truthed data collection can be facilitated using a truthed data collector 810 in communication with the cloud architecture 802 and an imaging system 812.

Figure 9:
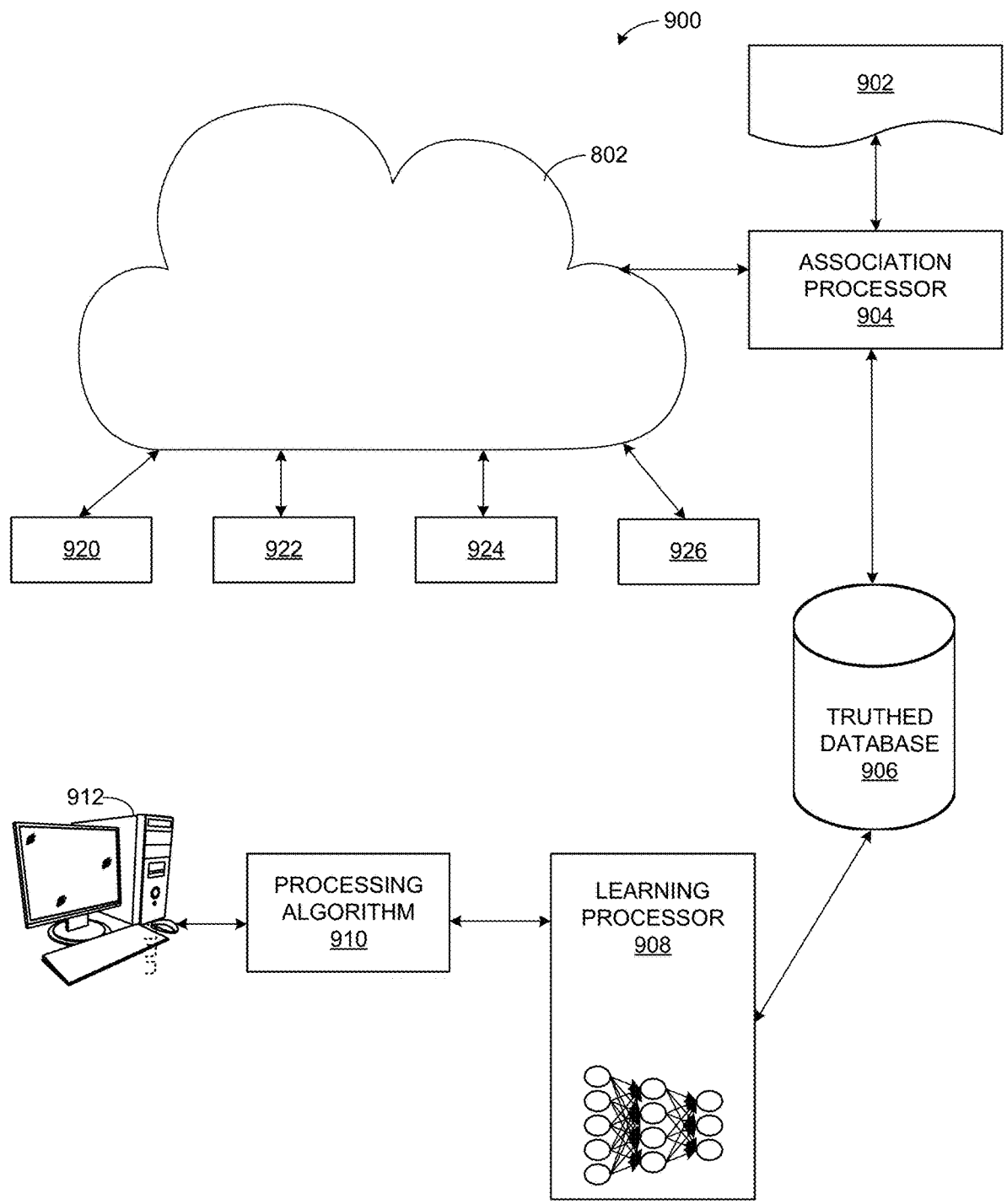
FIG. 9 illustrates an example system leveraging an example cloud architecture to generate a processing algorithm for processing of image data.

The example of cloud architecture 802 receives truthed data (e.g., images with or without localization of suspicious findings and/or other patient data, in association with available clinical outputs related to diagnosis, effect of treatment, or any other clinical outcome) from the truthed data collector 810. The truthed data can then be provided to the cloud architecture 802 such as for storage in the database 804, training/update of the network 806, output in the CAD performance report 808, etc. The truthed data collector 810, alone or in conjunction with the cloud architecture 802 (e.g., using the database 804, etc.) can establish a correlation between the patient data and the truth provided by the laboratory analyzer 814 and/or other processing/verification system. The laboratory analyzer 814 can verify, such as based on a tissue sample obtained from the patient, etc., that a computer-determined anomaly from the analysis of patient data, corresponds to a lesion, cancerous tissue, damage, etc. that can provide useful clinical information on the patient regarding diagnosis of disease and/or outcomes of treatments. For example, the analyzer 814 can verify that a biopsy confirmed identification of cancerous tissue where the CAD algorithm had identified suspicious findings in the image data from the imaging system 812. FIG. 9 illustrates an example system 900 leveraging the example cloud architecture 802 to generate a processing algorithm for CAD processing of image data, etc. As shown in the example of FIG. 9, a set of association rules 902 is provided to an association processor 904 (e.g., by transfer from another program, device, user, etc.). The association processor 904 can query and retrieve data from the cloud infrastructure 802 (e.g., based on the association rules 902, etc.). The association processor 904 can organize image and/or other data from the cloud 802 according to the association rules 902 to form a truthed database 906. The truthed database 906 can be used to train a learning processor 908. For example, the learning processor 908 can include a neural network and/or other machine learning construct (e.g., also referred to as a processing model herein) to be trained using data from the truthed database 906.

As shown in the example of FIG. 9, a plurality of inputs 920-926 can be provided to the cloud infrastructure 802. For example, demographics and risk factors 920, image reading and reporting 922, pathology result and reporting 924, treatment outcomes 926, etc., can be provided from one or more clinical systems to the cloud 802.

Using the association rules 902, for example, the association processor 904 can query the cloud 802 for data periodically (e.g., according to a schedule (e.g., nightly, daily, weekly, etc.), based on a trigger (e.g., new confirmed case received, etc.), and/or other criterion. The association module 904 can apply the rules 902 to organize the image data and/or other data such as demographics and risk factors 920, image reading and reporting 922, pathology result and reporting 924, treatment outcomes 926, etc., and correlating risk factors with image data and findings as well as pathology results and treatment outcomes to provide verified, "truthed" data to the database 906. The database 906 can be updated by the association processor 904 as new data is provided to the cloud 802, for example.

Examples of truthed data obtained after association of data in the cloud architecture 802 include input data and outcomes. Input data 920-924 can include demographic and/or risk factors, mammography, magnetic resonance, ultrasound or/and other image, radiologist report (e.g., location of findings, description of findings, etc.), breast density, tissue sample image, pathology report, initial visit oncologist report, follow-up visit oncologist report, etc. Outcomes 926 can include cancerous versus benign tissue, cancer grade, lesion localization, hormonal receptor status, treatment, clinical outcomes (e.g., cured, recurrence, death, etc.), etc.

The truthed database 906 can then be used by the learning processor 908 to update image data processing, for example. For example, the learning processor 908 can develop and/or update a processing model (e.g., using a neural network and/or other machine learning construct, etc.) to develop and/or update a processing algorithm 910 that can be applied to patient data to perform CAD on the patient data set. Thus, computer-aided decisions can be applied to a variety of patient data including image data, patient demographic data, metabolic data, risk factors, etc.

In certain examples, the processing algorithm 910 can correlate outputs with inputs (e.g., via training from the neural network and/or other machine learning from the learning processor 908, etc.). By correlating outputs with inputs, the processing algorithm 910 can, for example, detect lesions in an image, correlate input morphological information with output cancer grade, etc. For example, based on a shape of a potential lesion in input image data, the processing algorithm 910 can estimate a cancer grade associated with the lesion. The processing algorithm 910 can also correlate information from different input modalities knowing the output from the learning cases in the truthed database 906. The processing algorithm 910 can learn by knowing there is a lesion somewhere in the learning case without explicitly pointing out the lesion, for example. The processing algorithm 910 can be applied to image data provided by and/or displayed via a workstation, server, and/or other computing device 912, for example. The workstation 912 can facilitate user viewing, interaction, correction, and/or other feedback with respect to image data and/or other patient data in conjunction with CAD and/or other information provided by the processing algorithm 910, for example.

Thus, certain examples provide CAD algorithm(s) 910, improved through the application of artificial intelligence, to detect suspicious findings in clinical images such as mammography, etc. The CAD algorithm(s) 910 can process images and/or related information such as patient demographic data, prior examination data, etc. The workstation 912 can execute the CAD processing algorithm 910 to produce information such as CAD providing location of a suspicious area in an image as well as an associated grade/level of suspiciousness (e.g., probability of being an issue, etc.), etc.

For example, the CAD processing algorithm 910 is trained with data collected over a series of exams, cases, etc. For example, patient mammograms and associated truth (e.g., confirm location of cancerous tissue, type of cancerous tissue, other proven image finding, etc.) can be used to train the CAD algorithm 910 (e.g., based on deep learning (e.g., CNN, RNN, etc.), rule-based correlation (e.g., when processing this type of image with this type of algorithm can see this type of signal and that type of signal is usually of concern so we can flag this signal, etc.). Once the CAD algorithm 910 is trained from truthed cases of the database 906, the CAD processing algorithm 910 can be applied against another database including clinical data to verify that the CAD algorithm 910 can be extended to another truthed data set that was not involved in the training. In certain examples, the cloud database 804 serves as the training database, and the truthed database 906 serves as the verification database (and/or vice versa). Once tested, the CAD processing algorithm 910 can be deployed to a customer, such as via the workstation 912, etc.

Periodically (e.g., daily, weekly, on demand, triggered by availability, etc.), new information is provided through acquired images and truthed verification of patient outcomes. For example, a patient visits a hospital and has a mammography examination. Information is gathered by a receptionist and/or a nurse for the patient, and images are obtained from the mammography exam. A radiologist reads the acquired mammography images and recommends a biopsy for a suspicious area identified in an image. A pathologist provides biopsy results for that area and test results. The biopsy and/or other test result information can be used to continuously update the database 906 used to train the CAD algorithm 910, for example.

In certain examples, the association processor 904 processes hospital information (e.g., private server, cloud database, etc.) with a unique identifier for a particular patient (e.g., family history, images, test results, etc.) to tailor a particular processing algorithm 910 for the particular patient, type of patient, location, etc. The association processor 904 can process information from different departments and correlate the information for the particular patient to develop the CAD processing algorithm 910, for example. Demographics and/or associated risk factors 920, image reading/reporting 922, pathology result/report 924, treatment outcome 926, etc., can be gathered by the association processor 904 as the information becomes available for the particular patient (e.g., waiting for reading, waiting for pathology result, waiting for treatment outcome, etc.). The association processor 904 can then combine the information to update the truthed database 906 to train an updated model for the CAD processing algorithm 910. Updating the truthed database 906 enables updated biology, additional information, etc., to be factored into the algorithm 910 over time, for example.

In certain examples, the learning processor 908 updates the CAD algorithm 910 (e.g., using a processing model trained/updated according to truthed data, etc.) and makes correlations between collected data and a certain characteristic of a target patient. For example, the association processor 904 can determine that the patient is going to a doctor because he or she has diabetes. The learning processor 908 receives this association and can process information collected from the patient as well as the knowledge of diabetes to try to extract a probability of a patient having diabetes from the mammography image data. The learning processor 908 can correlate the probability of diabetes determination with oncology information to determine a likely/predict outcome of associated treatment. The learning processor 908 and associated algorithm 910 can then determine from the data the best available treatment option for diabetes given the type of available data.

Thus, in certain examples, the processing algorithm 910 can provide CAD as well as serve as a tool to propose a best treatment option for patients. The processing algorithm 910 can be general, specific to one hospital (e.g., all hospitals may not be providing the same type of treatment such as because of cost, etc.), and so on. Learning can be facilitated and reflected in the processing algorithm 910 in real time (or substantially real time given data processing, transmission, and/or storage latency, etc.) to update treatment based on performance for patient, hospital, etc.

Certain examples capture, associate, and build the database 906 in real time (or substantially real time given data processing, transmission, and/or storage latency, etc.). However, once the algorithm 910 is updated the system is to decide when the updated processing algorithm 910 is made available and/or otherwise deployed for use. For example, the updated CAD processing algorithm 910 can be deployed at night, when the system is not currently in active processing of a patient, etc. In certain examples, a few additional concepts and/or concerns are added to the database 906 every day, and the processing algorithm 910 is updated by the learning processor 908 daily and/or when a certain number of concepts/concerns have been gathered (e.g., 5, 10, etc.).

The learning processor 908 can update and/or otherwise process the CAD algorithm 910 via a neural network such as a CNN, etc., application of rules, use of decision trees (e.g., with hierarchical application of a set of rules, etc.), random forest (e.g., a network with many decision trees and outcomes of the different trees combined to make a decision, etc.), other processing model, etc.

Certain examples provide a hierarchy including a local solution while also contributing to a larger population (e.g., national, regional, consortium, etc.) solution. For example, the National Comprehensive Cancer Network consortium provides guidelines for treatment of cancer across the United States. The CAD processing algorithm 910 can be provided as a tool used at national level because many small (and large) hospitals can benefit from improved training materials. The algorithm 910 can be implemented on an external cloud and/or focused through a local server aggregating data from member sites, for example. Local learning schemes and/or high-level (e.g., regional, national, etc.) learning can be executed to provide solutions and support at varying levels and determine whether a larger result is applicable to one or more local sites and/or vice versa. In certain examples, the learning processor 908 can combine higher level with lower level results to generate the processing algorithm 910. In certain examples, the learning processor 908 can combine national and local results to provide more aggregated results reflected in the processing algorithm 910.

Certain examples analyze demographics, etc., to aggregate databases and sort databases to filter based on one or more parameters such as ethnicity, etc., so that a local hospital with a large ethnic population can look only at Hispanic people, for example, and train only on national data regarding a Hispanic population, for example, to generate the processing algorithm 910. Thus, national data satisfying a particular demographic can improve local algorithm 910 performance for a specific population and/or other criterion, for example. Databases can be aggregated and still be filterable on certain criterion, level, etc.

Software executing the processing algorithm 910 on a workstation 912 can be provided via the cloud 802 and/or deployed locally (e.g., to the workstation 912) after being trained with updated truthed data from the database 906. One hospital's installation may be different from other hospitals because of location, population, resource constraints, etc.

For example, image and/or other patient data can be pushed to the cloud 802 from the imaging system 812. A hospital/hospital network can be provided with a server 912 and/or network of servers (e.g., a five hospital network can be connected to one server that resides physically in one of the hospital buildings. A CAD system is installed on the server 912 with a capability to make associations (e.g., via the association processor 904 running on the server 912) such that data is sent from the five hospitals in the hospital network to the server 912 (e.g., in the fog adjacent to the cloud 802). The association processor 904 processes the data to update the truthed database 906 and perform a learning update via the learning processor 908 to update the processing cad algorithm 910 to be executed via the server 912. The cloud 802 can be a private cloud only accessible by the five hospitals in the hospital network, and the CAD processing algorithm 910 can also be specific to the network of five hospitals, for example.

Figure 10:
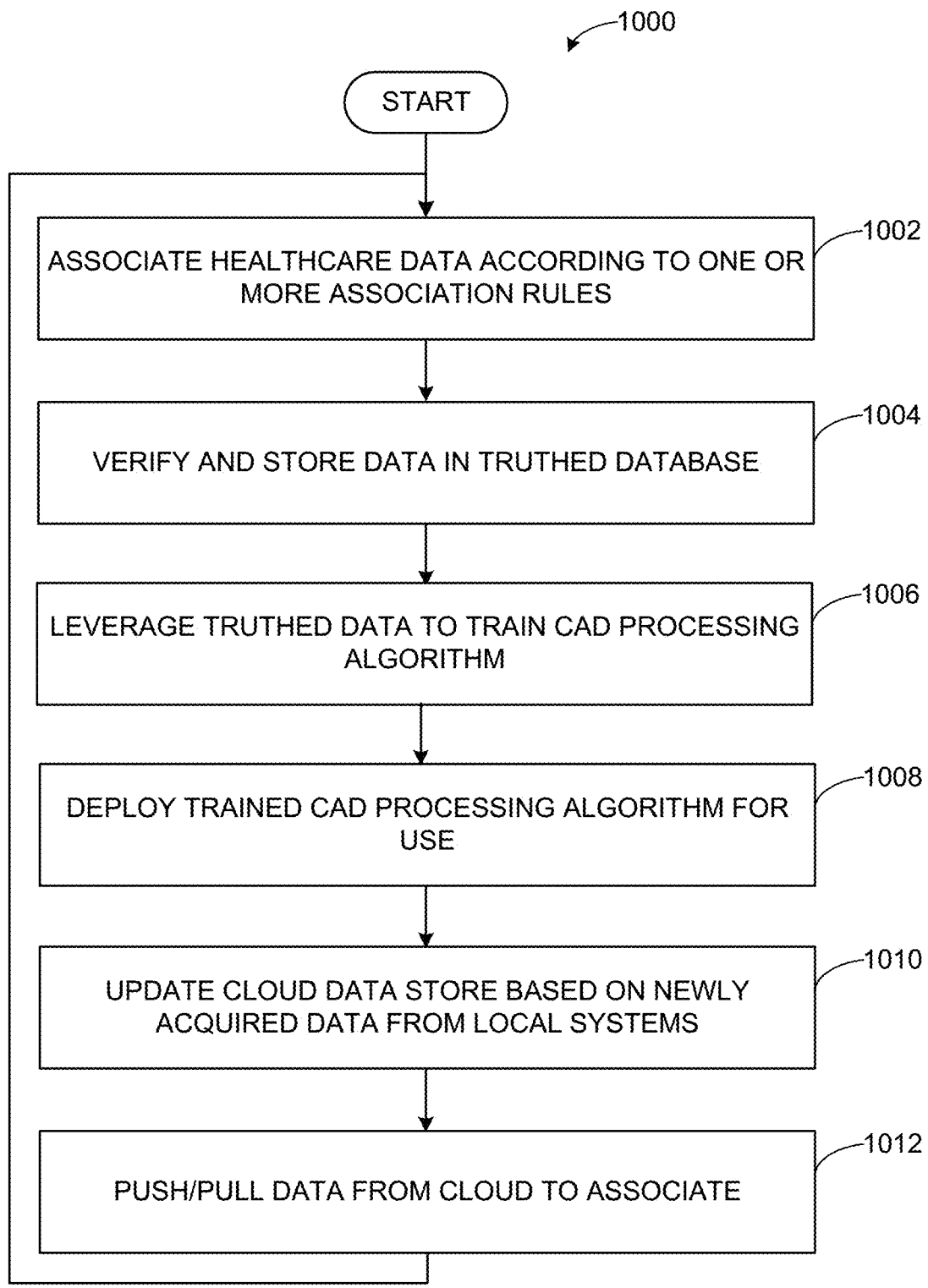
FIG. 10 illustrates a flow diagram of an example method to facilitate dynamic, customized computer-aided processing of patient image and/or other data.

FIG. 10 illustrates a flow diagram of an example method 1000 to facilitate a dynamic adaptation of CAD processing of patient image and/or other data based on truthed database updated over time through an association process leveraging information available in the cloud. At block 1002, image data, analysis data, and outcome data are associated by an association processor 904 according to one or more association rules 902. For example, the rules 902 can allow the processor 904 to correlate image data, analysis (e.g., radiology reading, etc.) data, and outcome data from the cloud 802.

An example association rule 902 includes to regroup all information related to one patient based on her/his unique identifier used in the hospital performing image acquisition, biological test, radiological or/and pathology reports, treatment prescription, etc. Another example association rule 902 includes to regroup all information related to one patient based on her/his last name and/or first name and/or birth date and/or social security number and/or other information which are usually considered as private information. Such association rules 902 enable regrouping patient information with patient outcomes (truthed data) and, therefore, improving the training of the CAD processing algorithm.

At block 1004, the data correlated by the association processor 904 is determined to be "truthed" or verified data and stored in the truthed database 906. That is, the association processor 904 matches image data and/or other patient data with outcome information to notify for example that an area noted in the image as suspicious was verified by biopsy to be cancerous tissue, etc. In another example, the association processor 904 matches patient data (e.g., including images and/or other patient data and/or clinical reports, etc.) and/or treatments prescribed to this patient with outcome information to notify, for example, that a particular treatment was beneficial to the health of the patient or, on the contrary, inefficient for patient care.

At block 1006, truthed data from the database 906 is leveraged by the learning processor 908 to train the CAD processing algorithm 910. For example, the learning processor 908 can configure the processing algorithm 910 to recognize image data elements, trends, probabilities, etc., particular to a given patient based on truthed information from the database 906 and one or more patient characteristics. For example, combining image data with lab results and information regarding a patient's high red blood cell counts and tendency to smoke can drive the CAD processing algorithm 910 in identifying diseased lung tissue. In another example, combining image data with biological test results on biopsy samples and information regarding a patient's body composition (e.g., fat fraction, and/or lean mass fraction, etc.) can drive the CAD processing algorithm 910 in identifying an appropriate dosage of drug in a chemotherapy course providing the highest treatment efficacy with the lowest level of toxicity.

At block 1008, the updated CAD processing algorithm 910 is deployed for use. For example, the algorithm 910 is deployed to a hospital server, workstation 912, etc., to be applied to input data such as image data, lab data, observation/examination data, and/or other patient data to determine a likely diagnosis (and potential care plan for actions to be taken and/or treatment) for a patient being examined.

While CAD process is usually focused on the detection of suspicious lesions in some body parts, the learning process based on truthed databases provides to the updated CAD a capability to adapt the course of action to be taken by the clinical practitioner at each step of the care pathway for a patient presenting a given pattern of information coming from images and/or other types of data. In a particular example, the truthed database, associating the outcome of different treatments (e.g., survival rate, number of months before recurrence, etc.) to different patterns of information collected on patients, enables selection of a particular treatment for a new patient presenting a pattern of information similar to a group of patients associated in the truthed database with positive outcomes after receiving this particular treatment (e.g., providing to the patient most appropriate treatment based on truthed information). In another example, the truthed database, associating the outcome of different imaging procedures (e.g., detection of satellite lesions close or at distance to the index lesion, extent of the lesion, composition of the lesion in some particular materials such as protein, water and lipid, contrast uptake related to the angiogenesis of the lesion, etc.) to different patterns of information collected on patients, enables to select a particular imaging test for a new patient presenting a pattern of information similar to a group of patients associated in the truthed database with positive outcomes after undertaking this particular imaging test (e.g., providing additional information by the selection of the most appropriate imaging test that will enable the practitioner to make the right decision based on truthed information, etc.).

At block 1010, the cloud 802 data store 804 is updated based on new patient data acquired from one or more local systems 810-814. The new/updated data from the data store 804 is used to update the machine learning network 806 and results 808. For example, participating clinicians, hospital networks, etc., can provide a nightly update of new patient-related data and/or updated outcome data that can be matched with prior image/patient data to verify or determine certain data to be "truthed" based on confirmation of an initial evaluation through a second source of verifiable information (e.g., confirming a CAD and/or radiologist identification of a lesion with lab data verifying the presence of the lesion in the tissue, etc.).

At block 1012, updated truthed data can be pushed and/or pulled by/from the cloud 802 to the association processor 904. Control then shifts to block 1002 for the association processor 904 to associate and/or otherwise process the updated information according to one or more association rules 902.

While example implementations are illustrated in conjunction with FIGS. 1-10, elements, processes and/or devices illustrated in conjunction with FIGS. 1-10 may be combined, divided, re-arranged, omitted, eliminated and/or implemented in any other way. Further, components disclosed and described herein can be implemented by hardware, machine readable instructions, software, firmware and/or any combination of hardware, machine readable instructions, software and/or firmware. Thus, for example, components disclosed and described herein can be implemented by analog and/or digital circuit(s), logic circuit(s), programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the components is/are hereby expressly defined to include a tangible computer readable storage device or storage disk such as a memory, a digital versatile disk (DVD), a compact disk (CD), a Blu-ray disk, etc. storing the software and/or firmware. Flowcharts representative of example machine readable instructions for implementing components disclosed and described herein are shown in conjunction with FIG. 10. In the examples, the machine readable instructions include a program for execution by a processor such as the processor 1112 shown in the example processor platform 1100 discussed below in connection with FIG. 11. The program may be embodied in machine readable instructions stored on a tangible computer readable storage medium such as a CD-ROM, a floppy disk, a hard drive, a digital versatile disk (DVD), a Blu-ray disk, or a memory associated with the processor 1112, but the entire program and/or parts thereof could alternatively be executed by a device other than the processor 1112 and/or embodied in firmware or dedicated hardware. Further, although the example program is described with reference to the flowchart illustrated in conjunction with at least FIG. 11, many other methods of implementing the components disclosed and described herein may alternatively be used. For example, the order of execution of the blocks may be changed, and/or some of the blocks described may be changed, eliminated, or combined. Although the flowchart of at least FIG. 10 depict example operations in an illustrated order, these operations are not exhaustive and are not limited to the illustrated order. In addition, various changes and modifications may be made by one skilled in the art within the spirit and scope of the disclosure. For example, blocks illustrated in the flowchart may be performed in an alternative order or may be performed in parallel.

As mentioned above, the example data structures and/or processes of at least FIGS. 1-10 can be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine readable storage medium" are used interchangeably. Additionally or alternatively, the example data structures and processes of at least FIGS. 1-10 can be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended. In addition, the term "including" is open-ended in the same manner as the term "comprising" is open-ended.

Figure 11:
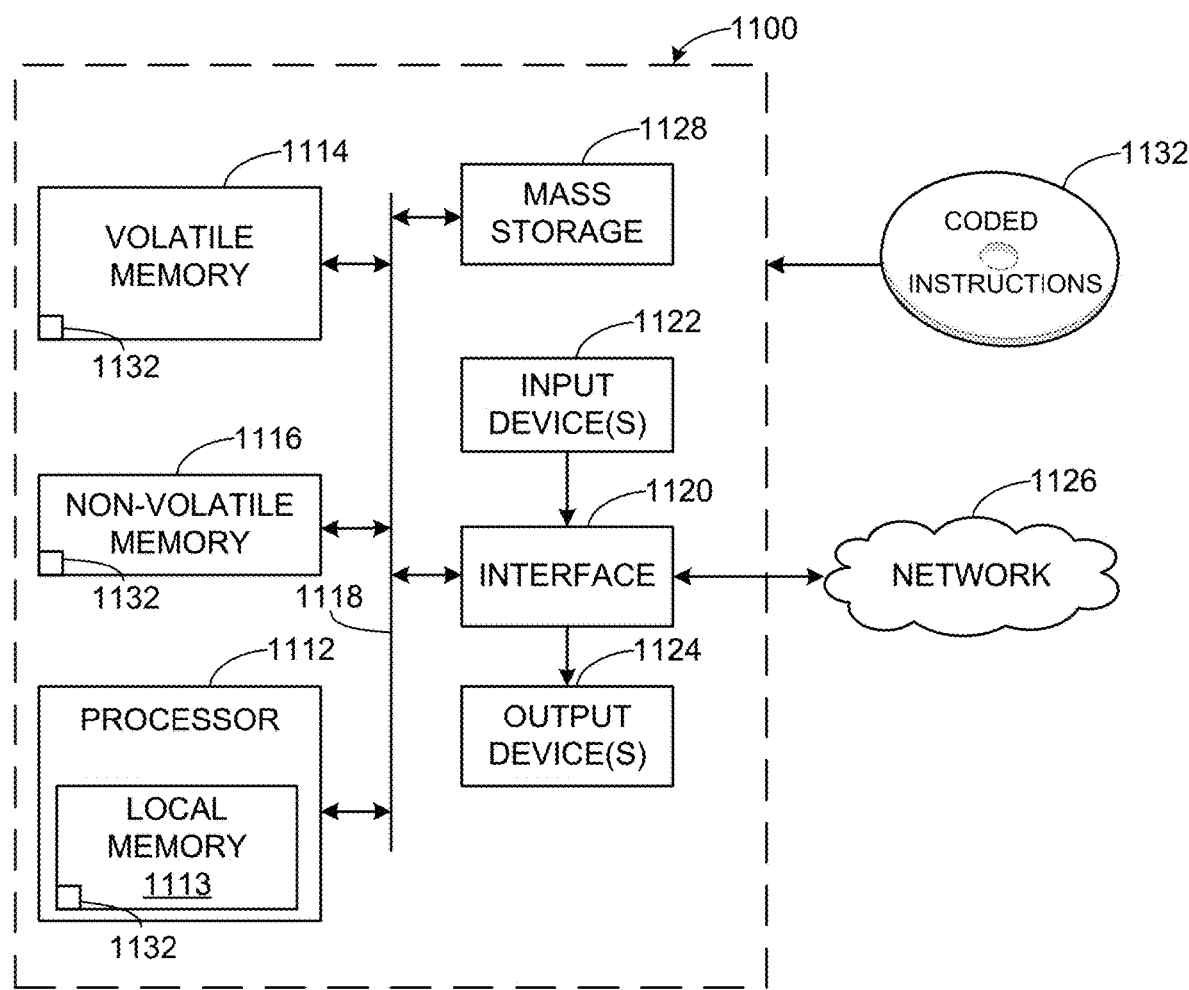
FIG. 11 is an example processor diagram which can be used to implement the methods and systems of FIGS. 1-10.

FIG. 11 is a block diagram of an example processor platform 1100 structured to executing the instructions of at least FIG. 10 to implement the example components disclosed and described herein. The processor platform 1100 can be, for example, a server, a personal computer, a mobile device (e.g., a cell phone, a smart phone, a tablet such as an iPad™), a personal digital assistant (PDA), an Internet appliance, or any other type of computing device.

The processor platform 1100 of the illustrated example includes a processor 1112. The processor 1112 of the illustrated example is hardware. For example, the processor 1112 can be implemented by integrated circuits, logic circuits, microprocessors or controllers from any desired family or manufacturer. The processor 1112 can be used to implement the example association processor 904 and/or the example learning processor 908, for example.

The processor 1112 of the illustrated example includes a local memory 1113 (e.g., a cache). The example processor 1112 of FIG. 11 executes the instructions of at least FIGS. 2-4 and 8 to implement the example systems 100, 800, 900, etc. The processor 1112 of the illustrated example is in communication with a main memory including a volatile memory 1114 and a non-volatile memory 1116 via a bus 1118. The volatile memory 1114 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 1116 may be implemented by flash memory and/or any other desired type of memory device. Access to the main memory 1114, 1116 is controlled by a clock controller.

The processor platform 1100 of the illustrated example also includes an interface circuit 1120. The interface circuit 1120 may be implemented by any type of interface standard, such as an Ethernet interface, a universal serial bus (USB), and/or a PCI express interface.

In the illustrated example, one or more input devices 1122 are connected to the interface circuit 1120. The input device(s) 1122 permit(s) a user to enter data and commands into the processor 1112. The input device(s) can be implemented by, for example, a sensor, a microphone, a camera (still or video), a keyboard, a button, a mouse, a touchscreen, a track-pad, a trackball, and/or a voice recognition system.

One or more output devices 1124 are also connected to the interface circuit 1120 of the illustrated example. The output devices 1124 can be implemented, for example, by display devices (e.g., light emitting diodes (LED), organic light emitting diodes (OLED), a liquid crystal display, a cathode ray tube display (CRT), a touchscreen, a tactile output device, and/or speakers). The interface circuit 1120 of the illustrated example, thus, typically includes a graphics driver card, a graphics driver chip or a graphics driver processor.

The interface circuit 1120 of the illustrated example also includes a communication device such as a transmitter, a receiver, a transceiver, a modem and/or network interface card to facilitate exchange of data with external machines (e.g., computing devices of any kind) via a network 1126 (e.g., an Ethernet connection, a digital subscriber line (DSL), a telephone line, coaxial cable, a cellular telephone system, etc.).

The processor platform 1100 of the illustrated example also includes one or more mass storage devices 1128 for storing software and/or data. Examples of such mass storage devices 1128 include floppy disk drives, hard drive disks, compact disk drives, Blu-ray disk drives, RAID systems, and digital versatile disk (DVD) drives.

The coded instructions 1132 of FIG. 11 may be stored in the mass storage device 1128, in the volatile memory 1114, in the non-volatile memory 1116, and/or on a removable tangible computer readable storage medium such as a CD or DVD.

From the foregoing, it will be appreciated that the above disclosed methods, apparatus, and articles of manufacture have been disclosed to create and dynamically update a CAD processing algorithm responsive to ongoing, cloud-based truthed feedback to generate a CAD processing algorithm tailored to particular patient characteristic(s) that can be used in patient simulation, analysis, diagnosis, and treatment to improve patient health outcome.

While image data has been used as an example throughout the description, it will be understood that a broader concept of patient data, including image data, can be processed according to systems and methods disclosed and described herein. That is, input data can include images and/or other type(s) of data related to the patient, such as patient history, family history, morphologic data, metabolic data, blood test results, genetic test results, etc., to which the computer-aided (clinical) decision algorithm can be applied.

Although certain example methods, apparatus and articles of manufacture have been described herein, the scope of coverage of this patent is not limited thereto. On the contrary, this patent covers all methods, apparatus and articles of manufacture fairly falling within the scope of the claims of this patent.

What is claimed is:

1. A method comprising:
    associating, using at least one processor, first patient data and first outcome data according to a set of association rules, the set of association rules to organize data retrieved from a cloud infrastructure according to at least one of patient, patient type, or location to form a truthed database;
    training, using the at least one processor, a processing model using machine learning to build the processing model using a machine learning network and the associated first patient data and first outcome data from the truthed database;
    generating, using the at least one processor, a computer-aided decision processing algorithm implemented using the processing model;
    dynamically updating, using the at least one processor, the computer-aided decision processing algorithm based on at least one of second patient data or second outcome data related to a patient characteristic of a target patient, the at least one of second patient data or second outcome data made available via the cloud infrastructure to combine with the truthed database to train an updated processing model; and
    deploying, using the at least one processor, the updated computer-aided decision processing algorithm to be applied to third patient data using the updated processing model of the updated computer-aided decision processing algorithm tailored to the target patient associated with the third patient data based on at least the patient characteristic of the target patient.

2. The method of claim 1, wherein the at least one processor includes an association processor and a learning processor.

3. The method of claim 1, wherein the first patient data includes first image data and the second patient data includes second image data.

4. The method of claim 1, wherein the at least one of second patient data or second outcome data is provided periodically by the cloud infrastructure after the at least one of second patient data or second outcome data is acquired and processed by the cloud infrastructure.

5. The method of claim 1, wherein the processing model includes an artificial neural network.

6. The method of claim 1, wherein the first patient data and the first outcome data are associated to provide truthed data when an analysis of the first patient data is confirmed by the first outcome data.

7. The method of claim 1, wherein associating further includes associating first demographic data and first pathology result data with the first patient data and the first outcome data.

8. A non-transitory computer readable medium including instructions which, when executed, cause at least one processor to at least:
    associate first patient data and first outcome data according to a set of association rules, the set of association rules to organize data retrieved from a cloud infrastructure according to at least one of patient, patient type, or location to form a truthed database;
    train a processing model using machine learning to build the processing model using a machine learning network and the associated first patient data and first outcome data from the truthed database;
    generate a computer-aided decision processing algorithm implemented using the processing model;
    dynamically update the computer-aided decision processing algorithm based on at least one of second patient data or second outcome data related to a patient characteristic of a target patient, the at least one of second patient data or second outcome data made available via the cloud infrastructure to combine with the truthed database to train an updated processing model; and
    deploy the updated computer-aided decision processing algorithm to be applied to third patient data using the updated processing model of the updated computer-aided decision processing algorithm tailored to the target patient associated with the third patient data based on at least the patient characteristic of the target patient.

9. The computer readable medium of claim 8, wherein the first patient data includes first image data and the second patient data includes second image data.

10. The computer readable medium of claim 8, wherein the at least one of second patient data or second outcome data is provided periodically by the cloud infrastructure after the at least one of second patient data or second outcome data is acquired and processed by the cloud infrastructure.

11. The computer readable medium of claim 8, wherein the processing model includes an artificial neural network.

12. The computer readable medium of claim 8, wherein the first patient data and the first outcome data are associated to provide truthed data when an analysis of the first patient data is confirmed by the first outcome data.

13. The computer readable medium of claim 8, wherein associating further includes associating first demographic data and first pathology result data with the first patient data and the first outcome data.

14. An apparatus including at least one processor and a memory, the memory including instructions which, when executed, cause the at least one processor to at least:
associate first patient data and first outcome data according to a set of association rules, the set of association rules to organize data retrieved from a cloud infrastructure according to at least one of patient, patient type, or location to form a truthed database;
train a processing model using machine learning to build the processing model using a machine learning network and the associated first patient data and first outcome data from the truthed database;
generate a computer-aided decision processing algorithm implemented using the processing model;
dynamically update the computer-aided decision processing algorithm based on at least one of second patient data or second outcome data related to a patient characteristic of a target patient, the at least one of second patient data or second outcome data made available via the cloud infrastructure to combine with the truthed database to train an updated processing model; and
deploy the updated computer-aided decision processing algorithm to be applied to third patient data using the updated processing model of the updated computer-aided decision processing algorithm tailored to the target patient associated with the third patient data based on at least the patient characteristic of the target patient.

15. The apparatus of claim 14, wherein the at least one processor includes an association processor and a learning processor.

16. The apparatus of claim 14, wherein the first patient data includes first image data and the second patient data includes second image data.

17. The apparatus of claim 14, wherein the at least one of second patient data or second outcome data is provided periodically by the cloud infrastructure after the at least one of second patient data or second outcome data is acquired and processed by the cloud infrastructure.

18. The apparatus of claim 14, wherein the processing model includes an artificial neural network.

19. The apparatus of claim 14, wherein the first patient data and the first outcome data are associated to provide truthed data when an analysis of the first patient data is confirmed by the first outcome data.

20. The apparatus of claim 14, wherein associating further includes associating first demographic data and first pathology result data with the first patient data and the first outcome data.

* * * * *